US005834010A

United States Patent [19]

Quan et al.

[11] Patent Number: 5,834,010
[45] Date of Patent: *Nov. 10, 1998

[54] TRIACETIN AS A PENETRATION ENHANCER FOR TRANSDERMAL DELIVERY OF A BASIC DRUG

[75] Inventors: Danyi Quan; Ninad A. Deshpanday; Srinivasan Venkateshwaran; Charles D. Ebert, all of Salt Lake City, Utah

[73] Assignee: Theratech, Inc., Salt Lake City, Utah

[*] Notice: The term of this patent shall not extend beyond the expiration date of Pat. No. 5,601,839.

[21] Appl. No.: 775,367

[22] Filed: Jan. 3, 1997

Related U.S. Application Data

[63] Continuation of Ser. No. 429,757, Apr. 26, 1995, Pat. No. 5,601,839.

[51] Int. Cl.⁶ .................................................. A61F 13/02
[52] U.S. Cl. ......................... 424/448; 424/449; 514/946
[58] Field of Search ..................................... 424/448, 449; 514/946

[56] References Cited

U.S. PATENT DOCUMENTS

| | | | |
|---|---|---|---|
| 4,414,222 | 11/1983 | Brooker | 424/270 |
| 4,666,926 | 5/1987 | Mahjour | 514/345 |
| 4,789,547 | 12/1988 | Song | 415/4.2 |
| 4,814,173 | 3/1989 | Song | 424/444 |
| 4,875,313 | 10/1989 | Song | 424/449 |
| 4,879,297 | 11/1989 | Mahjour | 514/282 |
| 4,895,727 | 1/1990 | Allen | 424/642 |
| 4,908,389 | 3/1990 | Mahjour | 514/772 |
| 5,019,395 | 5/1991 | Mahjour | 424/449 |
| 5,186,938 | 2/1993 | Sablotsky | 424/443 |
| 5,214,030 | 5/1993 | Stief | 514/12 |
| 5,482,970 | 1/1996 | Kim | 514/532 |

FOREIGN PATENT DOCUMENTS

| | | |
|---|---|---|
| 5-148141 | 6/1993 | Japan . |
| 93/09783 | 5/1993 | WIPO . |

*Primary Examiner*—D. Gabrielle Brouillette
*Attorney, Agent, or Firm*—Thorpe North & Western

[57] ABSTRACT

A composition and method for enhancing transdermal penetration of a basic drug are described. The composition comprises a matrix patch comprising an effective amount of a basic drug, preferably having a $pK_a$ of about 8.0 or greater, an effective amount of a penetration enhancer consisting essentially of triacetin, and a polymer layer preferably comprising a pressure-sensitive adhesive. A preferred basic drug is oxybutynin and acid addition salts thereof. The method for enhancing transdermal penetration comprises applying the matrix patch to a selected area of skin.

24 Claims, No Drawings

TRIACETIN AS A PENETRATION ENHANCER FOR TRANSDERMAL DELIVERY OF A BASIC DRUG

This application is a continuation of application Ser. No. 08/429,757 filed Apr. 26, 1995 now U.S. Pat. No. 5,601,839.

FIELD OF THE INVENTION

The present invention relates generally to a composition and method for enhancing the delivery of bioactive agents across biological membranes including skin or mucosa. More particularly, the invention relates to the use of triacetin (glyceryl triacetate) to enhance the transdermal or transmucosal delivery of a basic drug having a $pK_a$ of about 8.0 or greater, such as oxybutynin.

BACKGROUND OF THE INVENTION

The oral administration of drugs as currently employed is unsatisfactory for a number of reasons. First, drugs with short half lives require frequent dosing (2 to 4 times daily), which can lead to inadequate compliance by the patient. Second, the short plasma half life of the drug and frequent dosing regimen result in "peaks" and "valleys" in the plasma concentration profile, which increases the likelihood of adverse side effects associated with the peak concentration as well as lapse of therapeutic effectiveness toward the end of the dosing interval. Third, the potential effect of hepatic first pass metabolism associated with oral administration could lead to poor bioavailibility of the drug. Thus, an effective and consistent drug delivery system that overcomes these disadvantages would be far superior to the current oral regimen.

Transdermal delivery of drugs provides many advantages over conventional oral administration. Advantages of transdermal systems include convenience, uninterrupted therapy, improved patient compliance, reversibility of treatment (by removal of the system from the skin), elimination of "hepatic first pass" effect, a high degree of control over blood concentration of the drug, and improved overall therapy.

Although transdermal systems have many advantages, most drugs are not amenable to this mode of administration due to the well known barrier properties of the skin. Molecules moving from the environment into and through intact skin must first penetrate the stratum corneum, the outer horny layer of the skin, and any material on its surface. The molecule must then penetrate the viable epidermis and the papillary dermis before passing through the capillary walls and into systemic circulation. Along the way, each of the above-mentioned tissues will exhibit a different resistance to penetration by the same molecule. However, it is the stratum corneum, a complex structure of compact keratinized cell remnants separated by extracellular lipid domains, that presents the greatest barrier to absorption of topical compositions or transdermally administered drugs. Compared to the oral or gastric mucosa, the stratum corneum is much less permeable to outside molecules.

The flux of a drug across the skin can be increased by changing either (a) the resistance (the diffusion coefficient), or (b) the driving force (the solubility of the drug in the stratum corneum and consequently the gradient for diffusion). Many enhancer compositions have been developed to change one or both of these factors. U.S. Pat. Nos. 4,006,218; 3,551,154; and 3,472,931, for example, respectively describe the use of dimethylsulfoxide (DMSO), dimethyl formamide (DMF), and N,N-dimethylacetamide (DMA) for enhancing the absorption of topically applied drugs through the stratum corneum. Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol; and an inert diluent such as water.

Triacetin is known to be a solvent for solubilizing or diluting a drug and/or other components of drug delivery systems. For example, Mahjour et al., U.S. Pat. No. 4,879,297, disclose triacetin as a solvent in an enhancer system of propylene glycol and linoleic acid. Increasing amounts of triacetin and corresponding decreasing amounts of linoleic acid in the enhancer formulations correlate with decreasing flux and increasing lag time for permeation of the drug oxymorphone, suggesting that triacetin is relatively unimportant in the enhancer formulation. As another example, Ebert et al., WO9325168-A1, disclose triacetin as a solvent, in a list of many other solvents, to be used along with a cell-envelope disordering compound for the delivery of clonidine, progesterone, testosterone, and other drugs. Other patent documents that describe triacetin as a solvent include U.S. Pat. No. 4,908,389; U.S. Pat. No. 5,019,395; U.S. Pat. No. 4,666,926; U.S. Pat. No. 4,857,313; U.S. Pat. No. 4,789,547; U.S. Pat. No. 4,814,173; U.S. Pat. No. 4,783,450; EP-387647-A; JP63255227-A; JP62240628-A; and JP62215537-A.

Triacetin is also known as a plasticizer. For example, Edgren et al., U.S. Pat. No. 5,160,743, teach the use of triacetin as a conventional plasticizer to be used with an emulsifying agent in tablets, capsules, powders, and the like for gastrointestinal release of drugs. Other patent documents and publications that disclose use of triacetin as a plasticizer include Lin et al., 8 Pharm. Res. 1137 (1991); WO 9313753; EP 509335-A1; and JP3083917-A.

Triacetin has also been described to function as an anti-microbial agent. Allen, U.S. Pat. No. 4,895,727, teaches that triacetin has activity as an antifungal agent.

Triacetin has further been stated to contain activity as an absorption accelerator. Okuyama et al., WO9309783-A1, disclose a piroxicam-containing plaster for achieving an anti-inflammatory and analgesic effect due to absorption of piroxicam through the skin and state that triacetin enhances percutaneous absorption of piroxicam. The plaster is composed of a water-soluble polymeric adhesive; a glycol compound such as glycerin or propylene glycol; a cross-linking agent; water; an inorganic powder; and a surfactant, such as polyoxyethylene sorbitol monooleate, polyoxyethylene monooleate, sorbitol monooleate, or polyoxyethylene castor oil. It is further stated that, if necessary, penetration enhancers, preservatives, antioxidants, flavoring agents, and colorants can also be added to the formulation. The glycols and surfactants are classic solvents and cell-envelope disordering compounds known in the art of penetration enhancement, e.g. U.S. Pat. No. 4,855,294, thus the observed effects appear to result from the combination of glycol, surfactant, and triacetin.

Japanese patent document JP05148141-A describes a two-layer percutaneous absorption preparation containing an adhesive, isosorbide dinitrate, and an absorption accelerator. The absorption accelerators are stated to be glyceryl triesters wherein the fatty acid esters have chain lengths of 1 to 4 carbon atoms, triacetin being preferred. It should be recognized that isosorbide dinitrate has solubilizing properties of its own, i.e. it is a neutral, "solvent-acting drug," Sablotsky et al., U.S. Pat. No. 5,186,938. Other vasodilators, such as nitrate esters (—C—O—NO$_2$) characterized by a sequence of carbon-oxygen-nitrogen and nitrite esters characterized by a (—C—O—NO) sequence, are among these solvent-acting drugs, including glyceryl trinitrate (erroneously called nitroglycerin according to its widespread and official designation), mannitol hexanitrate, erythritol tetranitrate, and pentaerythritol tetranitrate. Thus, the penetration enhancing effect of triacetin reported by JP05148141-A is shown only in conjunction with a neutral, solvent-acting drug.

What has not been previously shown is that triacetin is by itself an effective penetration enhancer for promoting the transdermal delivery of non-solvent-acting drugs, particularly of basic drugs having a pK$_a$ of about 8.0 or greater and their acid addition salts. In view of the foregoing, it will be appreciated that compositions and methods for enhancing penetration of such basic drug and their acid addition salts would be a significant advancement in the art.

OBJECTS AND SUMMARY OF THE INVENTION

It is an object of the present invention to provide a composition and a method for enhancing percutaneous delivery of a basic drug through the skin or mucosa.

It is also an object of the invention to provide a composition and method for enhancing transdermal delivery of the basic drug oxybutynin or an acid addition salt thereof through the skin or mucosa.

It is another object of the invention to provide a composition and method for enhancing transdermal delivery of a basic drug having a pK$_a$ of 8.0 or greater, such as oxybutynin or an acid addition salt thereof, using triacetin as a penetration enhancer for permeating the skin or mucosa with the drug.

These and other objects are accomplished by providing a matrix patch for enhancing the rate of transdermal penetration of a basic drug having a pK$_a$ of about 8.0 or greater comprising (a) a biocompatible polymer layer;
(b) an effective amount of a percutaneously absorbable basic drug having a pK$_a$ of about 8.0 or greater; and
(c) an effective amount of a permeation enhancer consisting essentially of triacetin.

Preferred basic drugs having a pK$_a$ of 8.0 or greater include oxybutynin, scopolamine, fluoxetine, epinephrine, morphine, hydromorphone, atropine, cocaine, buprenorphine, chlorpromazine, imipramine, desipramine, methylphenidate, methamphetamine, lidocaine, procaine, pindolol, nadolol, carisoprodol, and acid addition salts thereof. Oxybutynin and acid addition salts thereof are particularly preferred. Preferably, the matrix patch comprises about 0.1% to about 50% by weight triacetin, more preferably about 1% to about 40% by weight triacetin, and most preferably about 2% to about 20% by weight triacetin. The polymer layer is preferably an adhesive, but can also be laminated to an adhesive layer or used with an overlay adhesive. Suitable polymers include acrylics, vinyl acetates, natural and synthetic rubbers, ethylenevinylacetate copolymers, polysiloxanes, polyacrylates, polyurethanes, plasticized weight polyether block amide copolymers, plasticized styrene-rubber block copolymers, and mixtures thereof. Acrylic copolymer adhesives are preferred. The matrix patch can also contain diluents, excipients, emollients, plasticizers, skin irritation reducing agents, carriers, and mixtures thereof provided that such additives do not alter the basic and novel characteristics of the matrix patch.

The method of enhancing transdermal penetration of a basic drug comprises applying the matrix patch described above to a selected application situs.

DETAILED DESCRIPTION OF THE INVENTION

Before the present composition and method for enhancing transdermal delivery of a basic drug, such as oxybutynin, and acid addition salts thereof are disclosed and described, it is to be understood that this invention is not limited to the particular process steps and materials disclosed herein as such process steps and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a drug delivery device containing "a drug" includes a mixture of two or more drugs, reference to "an adhesive" includes reference to one or more of such adhesives, and reference to "an excipient" includes reference to a mixture of two or more of such excipients.

In describing and claiming the present invention, the following terminology will be used in accordance with the definitions set out below.

As used herein, the terms "enhancement", "penetration enhancement" or "permeation enhancement" mean an increase in the permeability of a biological membrane (i.e. skin or mucosa) to a drug, so as to increase the rate at which the drug permeates through the membrane. "Permeation enhancer," "enhancer," "penetration enhancer," or similar term means a material that achieves such permeation enhancement, and an "effective amount" of an enhancer means an amount effective to enhance penetration through the skin or mucosa of a selected agent to a selected degree. The enhanced permeation as effected though the use of such enhancers can be observed, for example, by measuring the rate of diffusion of the drug through animal or human skin using a diffusion cell apparatus. Such a diffusion cell is described by Merritt et al., Diffusion Apparatus for Skin Penetration, 1 J. of Controlled Release 61 (1984), incorporated herein by reference.

As used herein, "transdermal" or "percutaneous" delivery means delivery of a drug by passage into and through the skin or mucosal tissue. Hence the terms "transdermal" and "transmucosal" are used interchangeably unless specifically stated otherwise. Likewise the terms "skin," "derma," "epidermis," "mucosa," and the like shall also be used interchangeably unless specifically stated otherwise.

By the term "permeant" or "drug" is meant any chemical material or compound suitable for transdermal or transmucosal administration which exists in the appropriate free base or acid addition salt form and induces a desired biological or pharmacological effect by transdermal delivery. Such substances include the broad classes of compounds normally delivered through body surfaces such as the skin. In general, this includes therapeutic agents in all of the major therapeutic areas including, but not limited to, anti-infectives such as antibiotics and antiviral agents, analgesics and analgesic combinations, anorexics, antidiarrheals, antihistamines, anti-inflammatory agents, antimigraine preparations, antimotion sickness agents, antinauseants, antineoplastics, antiparkinsonism drugs, antipruritics, antipsychotics, antipyretics, antispasmodics including gastrointestinal and urinary, anticholinergics, sympathomimetics, xanthine derivatives, cardiovascular preparations including calcium channel blockers, beta-blockers, antiarrythmics, antihypertensives, diuretics, vasodilators including general coronary, peripheral and cerebral, central nervous system stimulants including cough and cold preparations, decongestants, diagnostics, hormones, immunosuppressives, muscle relaxants, parasympatholytics, parasympathomimetics, psychostimulants, sedatives and tranquilizers. The term "permeant" or "drug" is also meant to include mixtures. By mixtures is meant combinations of permeants from different categories, mixtures of permeants from the same category, and mixtures of free base and salt forms of the same or different permeants from the same or different categories.

By "basic drug" is meant a drug or permeant that is a free base or an acid addition salt thereof. Preferred basic drugs contain an amino group that provides the drug with a basic character. More preferred are strongly basic drugs with a $pK_a$ of about 8.0 or greater. Preferred examples of basic drugs that can be delivered by the penetration enhancing system of the present invention include oxybutynin, scopolamine, fluoxetine, epinephrine, morphine, hydromorphone, atropine, cocaine, buprenorphine, chlorpromazine, imipramine, desipramine, methylphenidate, methamphetamine, lidocaine, procaine, pindolol, nadolol, carisoprodol, and acid addition salts thereof. Oxybutynin and acid addition salts thereof are more preferred.

By "effective amount" of a drug or permeant is meant a nontoxic but sufficient amount of a compound to provide the desired local or systemic effect. An "effective amount" of permeation enhancer as used herein means an amount selected so as to provide the desired increase in membrane permeability and, correspondingly, the desired depth of penetration, rate of administration, and amount of drug.

By "drug delivery system," "drug/enhancer composition," or any similar terminology is meant a formulated composition containing the drug to be transdermally delivered in combination with a penetration enhancer. Other pharmaceutically acceptable materials or additives can also be contained in the drug/enhancer composition, such as a diluent, skin-irritation reducing agent, carrier or vehicle, excipient, plasticizer, emollient, or other additive and mixtures thereof provided that such additives do not materially affect the basic and novel characteristics of the matrix patch.

By the term "matrix," "matrix system," or "matrix patch" is meant an active permeant or drug dissolved or suspended in a biocompatible polymeric phase, preferably a pressure sensitive adhesive, that can also contain other ingredients or in which the enhancer is also dissolved or suspended. This definition is meant to include embodiments wherein such polymeric phase is laminated to a pressure sensitive adhesive or used with an overlay adhesive. A matrix system usually and preferably comprises an adhesive layer having an impermeable film backing laminated onto the distal surface thereof and, before transdermal application, a release liner on the proximal surface of the adhesive. The film backing protects the polymeric phase of the matrix patch and prevents release of the drug and/or enhancer to the environment. The release liner functions similarly to the impermeable backing, but is removed from the matrix patch prior to application of the patch to an application situs. Matrix patches are known in the art of transdermal drug delivery to routinely contain such backing and release liner components, and matrix patches according to the present invention should be considered to comprise such backing and release liner or their functional equivalents. U.S. Pat. No. 5,122,383 describes such backing and release liner and is hereby incorporated by reference. A matrix system therefore is a unit dosage form of a drug composition in a polymeric carrier, also containing the enhancer and other components which are formulated for maintaining the drug composition in the polymeric layer in a drug transferring relationship with the derma, i.e. the skin or mucosa. A matrix patch is distinguished from a "liquid reservoir patch," wherein an active permeant or drug is dissolved in a gelled liquid contained in an occlusive device having an impermeable back surface and an opposite surface configured appropriately with a permeable membrane and adhesive for transdermal application. E.g., U.S. Pat. No. 4,983,395.

As used herein, "application situs" means a site suitable for topical application with or without the means of a mechanical sustained release device, patch, or dressing, e.g. behind the ear, on the arm, back, chest, abdomen, leg, top of foot, etc.

As described above, the present invention comprises a matrix patch for enhancing transdermal delivery of a basic drug having a $pK_a$ of about 8.0 or greater comprising (a) an biocompatible polymeric layer;

(b) an effective amount of a percutaneously absorbable basic drug having a $pK_a$ of about 8.0 or greater; and (c) an effective amount of a permeation enhancer consisting essentially of triacetin.

It is surprising and unexpected that triacetin is effective in enhancing transdermal penetration of basic drugs, particularly those having a $PK_a$ of about 8.0 or above, but not of neutral or acidic drugs. Of these basic drugs for which permeation is enhanced by triacetin, oxybutynin free base and acid addition salts thereof are preferred. It is further surprising that, although triacetin is effective as a penetration enhancer for basic drugs, such as oxybutynin free base, in matrix patch formulations, no penetration enhancement of basic drugs (including oxybutynin) or other drugs has been observed with liquid reservoir patches containing gelled drug formulations.

Suitable polymers that can be used in the biocompatible polymeric layer of the matrix patch include pressure-sensitive adhesives suitable for long-term contact with the skin. Such adhesives must be physically and chemically compatible with the drug and enhancer, and with any carriers and/or vehicles or other additives incorporated into the drug/enhancer composition. Suitable adhesives for use in the matrix patch include acrylic adhesives including cross-linked and uncross-linked acrylic copolymers; vinyl acetate adhesives; natural and synthetic rubbers including polyisobutylenes, neoprenes, polybutadienes, and polyisoprenes; ethylenevinylacetate copolymers; polysiloxanes;

polyacrylates; polyurethanes; plasticized weight polyether block amide copolymers, and plasticized styrene-rubber block copolymers. Preferred contact adhesives for use in the matrix patch herein are acrylic adhesives, such as TSR (Sekisui Chemical Co., Osaka, Japan) and DuroTak® adhesives (National Starch & Chemical Co., Bridgewater, N.J.), and polyisobutylene adhesives such as ARcare™ MA-24 (Adhesives Research, Glen Rock, Pa.).

In use, the matrix patch contains a distal backing laminated on the polymer layer. The distal backing defines the side of the matrix patch that faces the environment, i.e., distal to the skin or mucosa. The backing layer functions to protect the matrix polymer layer and drug/enhancer composition and to provide an impenetrable layer that prevents loss of drug to the environment. Thus, the material chosen for the backing should be compatible with the polymer layer, drug, and enhancer, and should be minimally permeable to any components of the matrix patch. Advantageously, the backing can be opaque to protect components of the matrix patch from degradation from exposure to ultraviolet light. Further, the backing should be capable of binding to and supporting the polymer layer, yet should be pliable to accommodate the movements of a person using the matrix patch. Suitable materials for the backing include metal foils, metalized polyfoils, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, and polypropylene. A thickness of about 0.0005 to 0.01 inch is preferred. The release liner can be made of the same materials as the backing, or other suitable films coated with an appropriate release surface.

The matrix patch can further comprise various additives in addition to the polymer layer, basic drug, and triacetin-containing penetration enhancer that are the fundamental components of the transdermal drug delivery system. These additives are generally those pharmaceutically acceptable ingredients that are known in the art of drug delivery and, more particularly, in the art of transdermal drug delivery provided that such additive ingredients do not materially alter the basic and novel characteristics of the matrix patch. For example, suitable diluents can include mineral oil, low molecular weight polymers, plasticizers, and the like. Many transdermal drug delivery formulations have a tendency to cause skin irritation after prolonged exposure to the skin, thus addition of a skin irritation reducing agent aids in achieving a composition that is better tolerated by the skin. A preferred skin irritation reducing agent is glycerin, U.S. Pat. No. 4,855,294. It is however notable that other so-called acceleration promoters or permeation enhancer components such as solvents and cell-envelope disordering compounds are not necessary, or even desired, in the present invention.

For delivery of the basic drug according to the present invention, the matrix patch device containing a polymer layer, basic drug such as oxybutynin, and triacetin-containing penetration enhancer is brought in contact with the skin or mucosa at a selected application situs and is held in place by a suitable pressure-sensitive adhesive. Preferably, the polymer layer of the matrix patch is an adhesive, but the polymer layer can also be laminated to an adhesive layer or used with an overlay adhesive.

It is to be understood that while the invention has been described in conjunction with the preferred specific embodiments thereof, that which follows is intended to illustrate and not limit the scope of the invention. Other aspects of the invention will be apparent to those skilled in the art to which the invention pertains.

Experimental

Skin Flux Studies

In vitro human cadaver skin flux studies were conducted using modified Franz non-jacketed permeation cells. The temperature of the cells was maintained at 32° C. by placing the cells in a circulating water bath positioned over a stirring module. The epidermal membrane was separated from the human cadaver whole skin by the heat-separation method of Kligman & Christopher, 88 Arch. Dermatol. 702 (1963), hereby incorporated by reference, involving treating the full thickness skin at 60° C. for 60 seconds, after which time the stratum corneum and the epidermis (epidermal membrane) were gently peeled from the dermis.

For skin flux studies of matrix devices, the epidermal membrane was cut into rectangular strips, and the matrix device was cut into 0.96 $cm^2$ circular discs. The release liner was peeled from the disc, and the disc was laminated onto the stratum corneum surface of the epidermal membrane to form a skin-matrix laminate. The skin-matrix laminate was then loaded between the donor and receiver compartments of a diffusion cell with the epidermal side facing the receiver compartment. The laminate was clamped in place, and the receiver compartment was then filled with an appropriate receiving solution for a selected drug. The receiving solution was selected such that the drug was stable in the solution, the subsequent assay of the drug was not interfered with, and solubility of the drug was adequate to ensure sink conditions throughout the experiment. The diffusion cell was then placed in a circulating water bath calibrated to maintain the skin surface temperature at 32°±1° C. At predetermined sampling intervals, the entire contents of the receiver compartment were collected for drug quantitation, and the receiver compartment was filled with fresh receiving solution, taking care to eliminate any air bubbles at the skin/solution interface.

For skin flux studies of gel formulations (i.e., for liquid reservoir patch designs), the epidermal membrane was cut and placed between two halves of the permeation cell with the stratum corneum facing the donor compartment. The skin was allowed to hydrate at 32° C. overnight with 0.02% (w/v) sodium azide solution in the receiver compartment. The following morning, 75 $\mu$l of a gelled formulation was placed into a cavity created by placing a polytetrafluoroethylene washer over the stratum corneum surface. The cavity was then occluded by clamping an occlusive backing over the washer and gel. An appropriate receiving solution for a selected drug was placed in the receiver compartment in contact with the dermal side of the epidermis. The solution in the receiver compartment was selected such that the drug was stable in the solution, the subsequent assay of the drug was not interfered with, and solubility of the drug was adequate to ensure sink conditions throughout the experiment. At predetermined sampling intervals, the entire contents of the receiver compartment were collected for drug quantitation and the receiver compartment was filled with fresh receiving solution, taking care to eliminate any air bubbles at the skin/solution interface.

The cumulative amount of drug permeating through the epidermal membrane, $Q_t$ ($\mu g/cm^2$), at any time t was determined from the following formula:

$$Q_t = \sum_{n=0}^{t} (C_n*V)/A$$

where $C_n$ is the concentration ($\mu g/ml$) of the drug in the receiver sample for the corresponding sample time, V is the volume of fluid in the receiver chamber (~6.3 cm$^3$), and A is the diffusional area of the cell (0.64 cm$^2$). The slope of the best fit line to the plot of $Q_t$ vs. t gives the steady state flux ($J_{ss}$, $\mu g/cm^2/hr$); the intercept of this line on the time axis give the lag time ($t_L$,h).

EXAMPLE 1

Oxybutynin free base, pKa=10.3, is a strongly basic drug administered transdermally for antispasmodic and anticholinergic therapy. Matrix patches containing varying amounts of oxybutynin free base and penetration enhancers were prepared and tested as described above. The matrix systems consisted of 5 to 20% by weight of oxybutynin free base and 0 to 20% by weight of the enhancer contained in a medical grade acrylic copolymer adhesive.

The matrix formulations were prepared as follows. First, the solids content of the adhesive was determined by weighing a small amount of the adhesive solution in a preweighed aluminum dish. The solvent was evaporated by overnight drying in a convection oven maintained at 80° C. and the weight of the residue (dry adhesive) and percent solid adhesive content of the solution were determined. Once the solids content was determined, a known weight of the acrylic copolymer adhesive solution was weighed into a glass bottle. From the weight of the adhesive solution and the percent solid adhesive content, the amount of adhesive in the solution was calculated. Oxybutynin free base and enhancer were added to the bottle in proportions to yield the selected final composition. The bottle was then tightly capped, sealed with laboratory film, and rotated overnight until all ingredients had completely dissolved and the resultant solution was visually clear.

Approximately 8 ml of the solution was then dispensed on a silanized polyester release liner and cast with a 10 mil gap casting knife. The casting was then dried in a convection oven at 70° C. for 15 minutes to evaporate the solvent and to yield a dried film approximately 0.002 inch thick. A 0.003 inch thick polyethylene backing film was laminated onto the dried adhesive film with a rubber roller. These matrix laminates were then used to conduct in vitro skin flux studies as described above. The results of the skin flux experiments are presented in Table 1–3.

TABLE 1

| Formulation[a] A/D/E (% w/w) | $Q_t$ (t = 24 hours) ($\mu g/cm^2/t$)[b] | $J_{ss}$ ($\mu g/cm^2/hr$)[b] |
| --- | --- | --- |
| 80/20/0 | 47.05 ± 21.01 | 2.03 ± 0.95 |
| 75/20/5 | 63.90 ± 23.45 | 3.07 ± 1.06 |
| 70/20/10 | 125.75 ± 56.00 | 6.08 ± 2.62 |
| 60/20/20 | 155.08 ± 74.55 | 7.46 ± 3.44 |

[a]A = adhesive = TSR; D = drug = oxybutynin; E = enhancer = triacetin
[b]Mean ± SD

TABLE 2

| Formulation[a] A/D/E (% w/w) | $Q_t$ (t = 24 hours) ($\mu g/cm^2/t$)[b] | $J_{ss}$ ($\mu g/cm^2/hr$)[b] |
| --- | --- | --- |
| 80/20/0 | 28.12 ± 13.74 | 1.13 ± 0.52 |
| 70/20/10 | 84.41 ± 30.72 | 3.64 ± 1.23 |
| 60/20/20 | 132.31 ± 42.61 | 5.92 ± 1.85 |

[a]A = adhesive = DuroTak 87-2196; D = drug = oxybutynin free base; E = enhancer = triacetin
[b]Mean ± SD

TABLE 3

| Formulation[a] A/D/E (% w/w) | $Q_t$ (t = 24 hours) ($\mu g/cm^2/t$)[b] | $J_{ss}$ ($\mu g/cm^2/hr$)[b] |
| --- | --- | --- |
| 85/15/0 | 61.57 ± 33.19 | 2.58 ± 1.39 |
| 75/15/10 | 135.36 ± 23.85 | 5.80 ± 0.90 |

[a]A = adhesive = ARcare MA-24; D = drug = oxybutynin free base; E = enhancer = triacetin
[b]Mean ± SD These results show that triacetin significantly increases the skin flux of oxybutynin free base as compared to adhesive/oxybutynin free base controls that lack triacetin. These enhancement effects by triacetin were observed with all three adhesives tested in these matrix formulations. With TSR adhesive at 20% drug loading, the increase is approximately 50% with 5% (w/w) triacetin, 3-fold with 10% (w/w) triacetin, and almost 4-fold with 20% (w/w) triacetin, as compared to controls. With DuroTak® 87-2196 adhesive at 20% drug loading, the increase in skin flux is about 3-fold with 10% (w/w) triacetin and 5-fold with 20% (w/w) triacetin, as compared to controls. With ARcare® MA-24 adhesive at 15% drug loading, a 2-fold increase in skin flux was observed with 10% (w/w) triacetin, as compared to controls.

EXAMPLE 2

The activity of several well known enhancers for enhancing transdermal flux of oxybutynin free base was evaluated according to the procedure of Example 1, with the exception that these enhancers were substituted for triacetin. The results of in vitro skin flux tests are shown in Table 4.

TABLE 4

| Enhancer | Formulation[a] A/D/E (% w/w) | $Q_t$ (t = 24 hours) ($\mu g/cm^2/t$)[b] | $J_{ss}$ ($\mu g/cm^2/hr$)[b] |
| --- | --- | --- | --- |
| None | 80/20/0 | 47.05 ± 21.01 | 2.03 ± 0.95 |
| Sorbitan Monooleate | 70/20/10 | 42.47 ± 21.63 | 1.92 ± 0.98 |
| N-methyl pyrrolidone | 60/20/20 | 54.36 ± 1.98 | 2.42 ± 0.97 |
| Lauryl alcohol | 70/20/10 | 24.29 ± 8.73 | 1.25 ± 0.41 |
| Isopropyl myristate | 70/20/10 | 48.26 ± 13.08 | 2.05 ± 0.54 |
| Glycerol monooleate | 70/20/10 | 52.78 ± 8.25 | 2.25 ± 0.32 |

[a]A = adhesive = TSR; D = drug = oxybutynin free base; E = enhancer
[b]Mean ± SD These results show that none of the well known penetration enhancers tested, sorbitan monooleate (ARLACEL 80, ICI Americas, Wilmington, Del.), N-methyl pyrrolidone (Pharmasolve®, International Specialty Chemicals, Wayne, N.J.), lauryl alcohol, isopropyl myristate, or glycerol monooleate, exhibited the ability to increase transdermal skin flux of the basic drug, oxybutynin free base, in a matrix system.

EXAMPLE 3

Piroxicam is a weakly basic anti-inflammatory, analgesic, and antipyretic agent with a pKa of 6.3. The activity of triacetin for enhancing transdermal flux of piroxicam was evaluated according to the procedure of Example 1, with the exception that piroxicam was substituted for oxybutynin. These results are shown in Table 5.

TABLE 5

| Expt. No. | Formulation[a] A/D/E (% w/w) | $Q_t$ (t = 24 hours) ($\mu g/cm^2/t$)[b] |
|---|---|---|
| 1 | 99.75/0.25/0 | 0.56 ± 0.30 |
|   | 99.25/0.25/0.5 | 0.58 ± 0.07 |
|   | 97.75/0.25/2.0 | 0.32 ± 0.08 |
|   | 95.75/0.25/4.0 | 0.45 ± 0.17 |
| 2 | 99.75/0.25/0 | 0.55 ± 0.31 |
|   | 99.25/0.25/0.5 | 0.27 ± 0.15 |
|   | 97.75/0.25/2.0 | 0.03 ± 0.02 |
|   | 95.75/0.25/4.0 | 0.18 ± 0.04 |
| 3 | 99.75/0.25/0 | 0.60 ± 0.20 |
|   | 99.25/0.25/0.5 | 0.36 ± 0.14 |
|   | 97.75/0.25/2.0 | 0.42 ± 0.09 |
|   | 95.75/0.25/4.0 | 0.31 ± 0.14 |

[a] A = adhesive = TSR; D = drug = piroxicam free base; E = enhancer = triacetin
[b] Mean ± SD These results show that triacetin decreases the skin flux of piroxicam. These results strongly suggest that the flux enhancement of piroxicam in gels, cited in Ikeda et al., WO 9309783-A1, is not due to triacetin alone, but appear to be a result of the combination of glycol and surfactants.

EXAMPLE 4

Liquid reservoir gel formulations containing oxybutynin free base and triacetin were tested as described above. Such liquid reservoir gel formulations were prepared in 10 ml quantities. Ethanol, water, glycerin, and triacetin were mixed in selected proportions in a capped vial. Then, 400 mg of oxybutynin free base was added to the vial, and the vial was capped and ultrasonicated to completely dissolve the drug. Next, 0.3 g of modified hydroxyethyl cellulose (NATROSOL PLUS 330CS, Aqualon, Wilmington, Del.) as a gelling agent was added to the mixture and the contents were mixed thoroughly and gently rotated overnight to completely dissolve the gelling agent. The resulting gel was then used in the skin flux studies, the results of which are presented in Table 6.

TABLE 6

| Expt No. | Formulation Et/W/G/E (% w/w)[a] | $Q_t$ (t = 24 hr) ($\mu g/cm^2/t$)[b] | $J_{ss}$ ($\mu g/cm^2/hr$)[b] |
|---|---|---|---|
| 1 | 30/60/10/0 | 178.41 ± 24.04 | 7.40 ± 0.98 |
|   | 30/58/10/2 | 191.54 ± 35.48 | 7.91 ± 1.48 |
|   | 30/50/10/10 | 110.58 ± 20.06 | 4.49 ± 0.83 |
| 2 | 30/60/10/0 | 172.41 ± 45.51 | 7.16 ± 1.89 |
|   | 30/58/10/2 | 144.05 ± 40.63 | 5.94 ± 1.68 |
|   | 30/50/10/10 | 155.74 ± 61.53 | 6.43 ± 2.60 |

TABLE 6-continued

| Expt No. | Formulation Et/W/G/E (% w/w)[a] | $Q_t$ (t = 24 hr) ($\mu g/cm^2/t$)[b] | $J_{ss}$ ($\mu g/cm^2/hr$)[b] |
|---|---|---|---|
| 3 | 30/60/10/0 | 118.23 ± 52.30 | 4.86 ± 2.15 |
|   | 30/58/10/2 | 65.27 ± 10.81 | 2.65 ± 0.44 |
|   | 30/50/10/10 | 54.75 ± 12.91 | 2.22 ± 0.52 |

[a] Et = ethanol; W = water; G = glycerin; E = enhancer = triacetin
[b] Mean ± SD These results show that triacetin does not enhance the flux of oxybutynin from a gel formulation such as could be used in a liquid reservoir device. The flux actually decreases with triacetin-containing systems, consistent with Mahjour et al., U.S. Pat. No. 4,879,297. Thus, even though triacetin very effectively enhances penetration of oxybutynin from matrix formulations, triacetin fails to enhance penetration of the same drug from reservoir formulations.

EXAMPLE 5

The following formulations are exemplary of other compositions within the scope of this invention with triacetin and other highly basic active permeants in matrix patches. Such matrix patches can be made according to the procedure of Example 1. Several different types of pressure sensitive, skin-contacting, medical grade adhesives can be used, such as acrylic copolymer adhesives or "acrylic adhesive" (e.g., DuroTak 80-1196, National Starch; Gelva 737, Monsanto Co., St. Louis, Mo.), rubber based adhesives or "rubber adhesive" such as polyisobutylene or "PIB adhesive" (e.g., Adhesive Research MA-24), and silicone based adhesives or "silicone adhesive" such as Dow Bio-PSA. All compositions are given in ranges expressed in in percent by weight.

| | |
|---|---|
| Formulation 5-A | |
| Morphine | 0.1–2.5% |
| Acrylic Adhesive | 82.5–94.9% |
| Triacetin | 5.0–15.0% |
| Formulation 5-B | |
| Hydromorphone | 30.0–40.0% |
| PIB Adhesive | 55.0–68.0% |
| Triacetin | 2.0–20.0% |
| Formulation 5-C | |
| Scopolamine | 2.0–10.0% |
| PIB Adhesive | 75.0–93.0% |
| Triacetin | 5.0–15.0% |
| Formulation 5-D | |
| Atropine | 1.0–10.0% |
| Silicone Adhesive | 85.0–98.0% |
| Triacetin | 1.0–5.0% |
| Formulation 5-E | |
| Cocaine | 0.5–5.0% |
| Acrylic Adhesive | 80.0–94.5% |
| Triacetin | 5.0–15.0% |
| Formulation 5-F | |
| Buprenorphine | 0.5–5.0% |
| PIB Adhesive | 85.0–97.0% |
| Triacetin | 2.5–10.0% |
| Formulation 5-G | |
| Scopolamine | 0.1–5.0% |
| Acrylic Adhesive | 90.0–96.4% |
| Triacetin | 1.0–5.0% |

-continued

| | |
|---|---|
| Formulation 5-H | |
| Chlorpromazine | 0.5–7.5% |
| Acrylic Adhesive | 78.5–94.5% |
| Triacetin | 1.0–20.0% |
| Formulation 5-I | |
| Imipramine | 0.5–5.0% |
| Acrylic Adhesive | 85.0–97.0% |
| Triacetin | 2.5–10.0% |
| Formulation 5-J | |
| Desipramine | 0.5–5.0% |
| Acrylic Adhesive | 87.5–94.0% |
| Triacetin | 2.5–7.5% |
| Formulation 5-K | |
| Methylphenidate | 0.1–1.0% |
| Silicone Adhesive | 94.0–97.4% |
| Triacetin | 2.5–5.0% |
| Formulation 5-L | |
| Methamphetamine | 2.5–10.0% |
| Acrylic Adhesive | 82.5–95.0% |
| Triacetin | 2.5–7.5% |
| Formulation 5-M | |
| Lidocaine | 0.1–5.0% |
| Acrylic Adhesive | 90.0–98.9% |
| Triacetin | 1.0–5.0% |
| Formulation 5-N | |
| Procaine | 0.1–5.0% |
| PIB Adhesive | 80.0–97.4% |
| Triacetin | 2.5–15.0% |
| Formulation 5-O | |
| Pindolol | 0.1–10.0% |
| Acrylic Adhesive | 65.0–94.9% |
| Triacetin | 5.0–25.0% |
| Formulation 5-P | |
| Nadolol | 0.1–10.5% |
| Acrylic Adhesive | 74.5–94.9% |
| Triacetin | 5.0–15.0% |
| Formulation 5-Q | |
| Fluoxetine | 5.0–40.0% |
| Acrylic Adhesive | 35.0–84.9% |
| Triacetin | 5.0–25.0% |
| Formulation 5-R | |
| Fluoxetine | 5.0–40.5% |
| PIB Adhesive | 55.5–90.0% |
| Triacetin | 5.0–15.0% |
| Formulation 5-S | |
| Fluoxetine | 5.0–40.5% |
| Silicone Adhesive | 55.5–89.5% |
| Triacetin | 5.0–15.0% |
| Formulation 5-T | |
| Fluoxetine | 5.0–40.5% |
| EVA copolymer | 55.5–89.5 |
| Triacetin | 5.0–15.0% |
| Formulation 5-U | |
| Fluoxetine | 5.0–40.5% |
| Styrene-Rubber Block Copolymer | 55.5–89.5% |
| Triacetin | 5.0–15.0% |
| Formulation 5-V | |
| Carisoprodol | 5.0–40.5% |
| PIB Adhesive | 55.5–89.5% |
| Triacetin | 5.0–15.0% |

We claim:

1. A method of enhancing the rate of transdermal penetration of a basic drug having a $pK_a$ of about 8.0 or greater comprising applying to a selected application situs a matrix patch comprising
   (a) a biocompatible polymer layer, wherein said biocompatible polymer is a pressure sensitive adhesive selected from the group consisting of acrylics, vinyl acetates, natural and synthetic rubbers, ethylenevinylacetate copolymers, polysiloxanes, polyacrylates, polyurethanes, plasticized polyether block amide copolymers, plasticized styrene-rubber block copolymers, and mixtures thereof;
   (b) an effective amount of a percutaneously absorbable basic drug having a $pK_a$ of about 8.0 or greater; and
   (c) an effective amount of a permeation enhancer consisting essentially of triacetin.

2. The method of claim 1 wherein said basic drug is a member selected from the group consisting of oxybutynin, scopolamine, fluoxetine, epinephrine, morphine, hydromorphone, atropine, cocaine, buprenorphine, chlorpromazine, imipramine, desipramine, methylphenidate, methamphetamine, lidocaine, procaine, pindolol, nadolol, carisoprodol, and acid addition salts thereof.

3. The method of claim 2 wherein said effective amount of permeation enhancer comprises about 0.1% to about 50% by weight of triacetin.

4. The method of claim 3 wherein said basic drug is a member selected from the group consisting of oxybutynin and acid addition salts thereof.

5. The method of claim 4 wherein said effective amount of permeation enhancer comprises about 1% to about 40% by weight of triacetin.

6. The method of claim 5 wherein matrix patch further comprises a member selected from the group consisting of diluents, excipients, emollients, plasticizers, skin irritation reducing agents, carriers, and mixtures thereof.

7. The method of claim 6 wherein said basic drug is oxybutynin.

8. The method of claim 7 wherein said adhesive is an acrylic copolymer.

9. The method of claim 8 wherein the permeation enhancer comprises about 2% to about 20% by weight of triacetin.

10. The method of claim 9 wherein said matrix patch comprises a skin irritation reducing agent, wherein said skin irritation reducing agent is glycerin.

11. The method of claim 3 wherein said polymer layer is laminated to an adhesive.

12. The method of claim 3 wherein said polymer layer is overlaid with an adhesive.

13. A matrix patch for transdermal administration of a basic drug having a $pK_a$ of about 8.0 or greater comprising
   (a) a biocompatible polymer layer, wherein said biocompatible polymer is a pressure sensitive adhesive selected from the group consisting of acrylics, vinyl acetates, natural and synthetic rubbers, ethylenevinylacetate copolymers, polysiloxanes, polyacrylates, polyurethanes, plasticized polyether block amide copolymers, plasticized styrene-rubber block copolymers, and mixtures thereof;
   (b) an effective amount of a percutaneously absorbable basic drug having a $pK_a$ of about 8.0 or greater; and
   (c) an effective amount of a permeation enhancer consisting essentially of triacetin.

14. The matrix patch of claim 13 wherein said basic drug is a member selected from the group consisting of oxybutynin, scopolamine, fluoxetine, epinephrine, morphine, hydromorphone, atropine, cocaine, buprenorphine, chlorpromazine, imipramine, desipramine, methylphenidate, methamphetamine, lidocaine, procaine, pindolol, nadolol, carisoprodol, and acid addition salts thereof.

15. The matrix patch of claim 14 wherein said effective amount of permeation enhancer comprises about 0.1% to about 50% by weight of triacetin.

16. The matrix patch of claim 15 wherein said basic drug is a member selected from the group consisting of oxybutynin and acid addition salts thereof.

17. The matrix patch of claim 16 wherein said effective amount of permeation enhancer comprises about 1% to about 40% by weight of triacetin.

18. The matrix patch of claim 17 wherein matrix patch further comprises a member selected from the group consisting of diluents, excipients, emollients, plasticizers, skin irritation reducing agents, carriers, and mixtures thereof.

19. The matrix patch of claim 18 wherein said basic drug is oxybutynin.

20. The matrix patch of claim 19 wherein said adhesive is an acrylic copolymer.

21. The matrix patch of claim 20 wherein the permeation enhancer comprises about 2% to about 20% by weight of triacetin.

22. The matrix patch of claim 21 wherein said matrix patch comprises a skin irritation reducing agent, wherein said skin irritation reducing agent is glycerin.

23. The matrix patch of claim 15 wherein said polymer layer is laminated to an adhesive.

24. The matrix patch of claim 15 wherein said polymer layer is overlaid with an adhesive.

* * * * *